US009395296B1

(12) United States Patent
Milton et al.

(10) Patent No.: US 9,395,296 B1
(45) Date of Patent: Jul. 19, 2016

(54) TWO-DIMENSIONAL OPTICAL SPOT LOCATION USING A ONE-DIMENSIONAL DETECTOR ARRAY

(71) Applicant: United States of America, as represented by the Secretary of the Army, Washington, DC (US)

(72) Inventors: Albert Fenner Milton, Alexandria, VA (US); Stephen R. Chinn, Alexandria, VA (US); Lew Goldberg, Fairfax, VA (US)

(73) Assignee: THE UNITED STATES OF AMERICA, AS REPRESENTED BY THE SECRETARY OF THE ARMY, Washington, DC (US)

( * ) Notice: Subject to any disclaimer, the term of this patent is extended or adjusted under 35 U.S.C. 154(b) by 0 days.

(21) Appl. No.: 14/627,819

(22) Filed: Feb. 20, 2015

(51) Int. Cl.
| | | |
|---|---|---|
| *G01N 21/63* | (2006.01) | |
| *G01N 33/483* | (2006.01) | |
| *G01N 21/47* | (2006.01) | |
| *G01N 21/49* | (2006.01) | |
| *G01S 17/89* | (2006.01) | |

(Continued)

(52) U.S. Cl.
CPC ............... *G01N 21/47* (2013.01); *G01N 21/49* (2013.01); *G01N 21/63* (2013.01); *G01S 17/06* (2013.01); *G01S 17/08* (2013.01); *G01S 17/89* (2013.01); *G02B 6/06* (2013.01); *G02B 6/065* (2013.01); *G02B 6/10* (2013.01); *G01N 2201/06113* (2013.01)

(58) Field of Classification Search
CPC ............... A61B 1/00142; A61B 1/31; A61B 2562/0233; A61B 2562/0242; A61B 2562/043; A61B 5/0066; A61B 5/0086; A61B 5/14532; A61B 5/1455; G01N 2021/646; G01N 21/49; G01N 21/63; G01N 21/64; G01N 2201/02; G01N 2201/06113; G01N 33/4833; G01S 13/723; G01S 13/86; G01S 13/867; G01S 13/87; G01S 13/931; G01S 17/023; G01S 2013/9321; G01S 2013/9325; G01S 2013/9342; G01S 2013/9346; G01S 2013/935; G01S 2013/9353; G01S 2013/9357; G01S 2013/936; G01S 2013/9375; G01S 17/89; G01S 17/06; G01S 17/08; G02B 2027/014; G02B 26/10; G02B 27/01; G02B 6/06; G02B 6/065; G02B 6/10
See application file for complete search history.

(56) References Cited

U.S. PATENT DOCUMENTS

| 4,975,729 A | 12/1990 | Gordon |
| 5,337,325 A | 8/1994 | Hwang |

(Continued)

FOREIGN PATENT DOCUMENTS

WO 2009020450 A1 2/2009

OTHER PUBLICATIONS

Web publication, "SU1024LE InGaAs Linear Photodiode Array detector array," 1024LE Array by Sensors Unlimited, Inc., Apr. 2003, http://www.stellarnet-inc.com/public/download/1024LE-Series%20Array%20REV%204_03.pdf.

*Primary Examiner* — Dionne H Pendleton
(74) *Attorney, Agent, or Firm* — Richard J. Kim

(57) ABSTRACT

An optical detector array is disclosed to locate dynamically the source position of an incoming beam of light. For example, the incoming beam of light may be a reflection of a low-divergence laser beam from a scattering surface in target space. A system and a method are disclosed for determining the position of a light spot generated by an optical beam when it falls on a scattering surface based on a one-dimensional detector array.

17 Claims, 6 Drawing Sheets

(51) Int. Cl.
*G01S 17/06* (2006.01)
*G01S 17/08* (2006.01)
*G02B 6/06* (2006.01)
*G02B 6/10* (2006.01)

(56) References Cited

U.S. PATENT DOCUMENTS

| | | | |
|---|---|---|---|
| 6,353,226 B1 * | 3/2002 | Khalil | A61B 5/14532 250/339.11 |
| 7,242,468 B1 | 7/2007 | Zhang | |
| 7,626,696 B2 | 12/2009 | Zhang | |
| 8,493,573 B2 | 7/2013 | Chinn et al. | |
| 2007/0134615 A1 * | 6/2007 | Lovely | A61B 5/0088 433/29 |
| 2010/0253688 A1 * | 10/2010 | Cui | G01S 13/723 345/443 |
| 2015/0177383 A1 * | 6/2015 | Ruff | G01S 17/89 356/4.01 |
| 2015/0320319 A1 * | 11/2015 | Alfano | A61B 5/0086 600/425 |
| 2015/0346095 A1 * | 12/2015 | Jeon | G01N 21/64 250/458.1 |

\* cited by examiner

TWO-DIMENSIONAL OPTICAL SPOT LOCATION USING A ONE-DIMENSIONAL DETECTOR ARRAY

GOVERNMENT INTEREST

The invention described herein may be manufactured, used, sold, imported, and/or licensed by or for the Government of the United States of America.

FIELD OF THE INVENTION

This invention relates in general to optics, and more particularly, to optical detector arrays.

BACKGROUND OF THE INVENTION

The present disclosure addresses a system and a method to dynamically locate the source position of an incoming beam of light generated by the reflection of a low-divergence laser beam from a scattering surface in target space.

SUMMARY OF THE INVENTION

A method for determining the position of a detected light spot from an optical beam incident on a scattering surface is disclosed using a linear optical detector array.

In one aspect, a method is disclosed for determining the position of a light spot generated by an optical beam when it falls on a scattering surface using a detector array. Such a method is comprised of the steps of emitting light from a laser source towards a surface to reflect and backscatter the emitted light incident on the surface; focusing said backscattered light incident on a lens to a spot in a focal plane of the lens; disposing a fiber bundle with its input end near the focal plane of the lens; placing a detector array against an output end of the fiber bundle outputting 2D intensity distribution in the focal plane to produce a corresponding set of electrical signals; electronic signal processing the set of electrical signals to provide high-resolution spot location, wherein a position of the focused spot formed by the lens is determined based on finding a centroid of a set of the brightest illuminated pixels of the detector array; a bore-sight aligned camera providing a context image; and displaying the location of the spot on a display of said context image based on said electronic signal processing of said set of electrical signals.

In another aspect, a system is disclosed for determining the position of a light spot generated by an optical beam when it falls on a scattering surface. Such a system is comprised of a laser source for emitting light towards a surface to reflect and backscatter the emitted light; a lens disposed to focus said backscattered light to a spot in a focal plane of the lens; a fiber bundle with its input end disposed near the focal plane of the lens, an output end of the fiber bundle being arranged to output a 2D intensity distribution in the focal plane mapped to a linear geometry at its output end; a linear detector array disposed to mate with said output end of the fiber bundle and output one-dimensional linear array data as a set of signals that represent the intensity distribution in the focal plane of the lens; an electronic signal processor to process the one-dimensional linear array data for high-resolution spot location; and a display for imaging said surface in an x-y position display field of view. A position of the spot is indicated by a marker icon on the display based on the processed one-dimensional linear array data.

Yet, in another aspect, a system for determining the position of a light spot is disclosed based on a hexagonal close-packed fiber array. Such a system is comprised of a lens disposed to focus light to a focal plane of the lens; a hexagonal close-packed fiber array with its input end disposed near the focal plane of the lens, wherein pairs of adjacent fibers at the input end form micro-bundles to output an image in the focal plane mapped to a linear geometry of sequenced micro-bundles at its output end; and a linear detector array disposed to mate with said linear geometry of sequenced micro-bundles, wherein a pair of fibers at the output end couples to a respective set of sequential pixels of said linear detector array to output one-dimensional linear array data in sets of sequential pixels as an image signal output for electronic signal processing to determine the position of the light spot.

BRIEF DESCRIPTION OF THE DRAWINGS

Additional advantages and features will become apparent as the subject invention becomes better understood by reference to the following detailed description when considered in conjunction with the accompanying drawings wherein.

DETAILED DESCRIPTION

A method and a system for determining the position of a light spot generated by an optical beam when it falls on a scattering surface is disclosed.

Figure 1A:
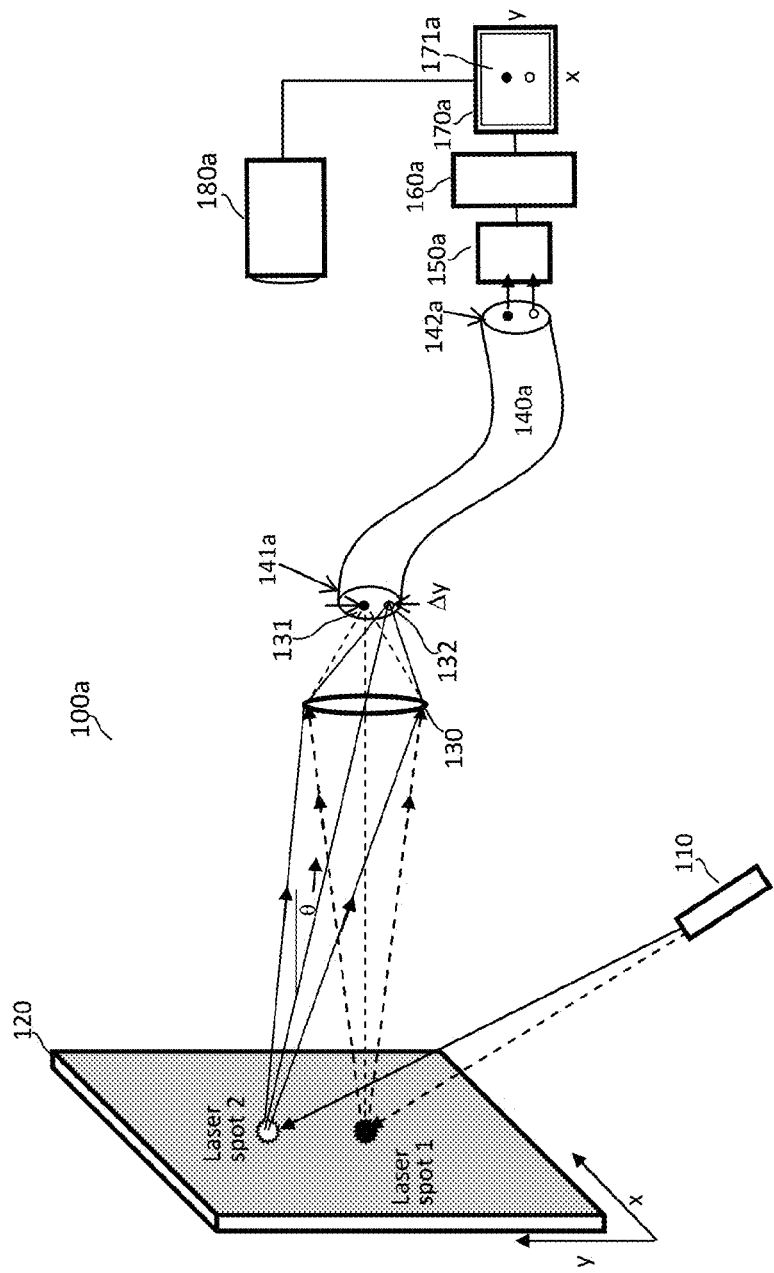
FIG. 1a shows a block diagram of an exemplary system for determining location of a light spot on a surface using a two-dimensional detector FPA.
Figure 1B:
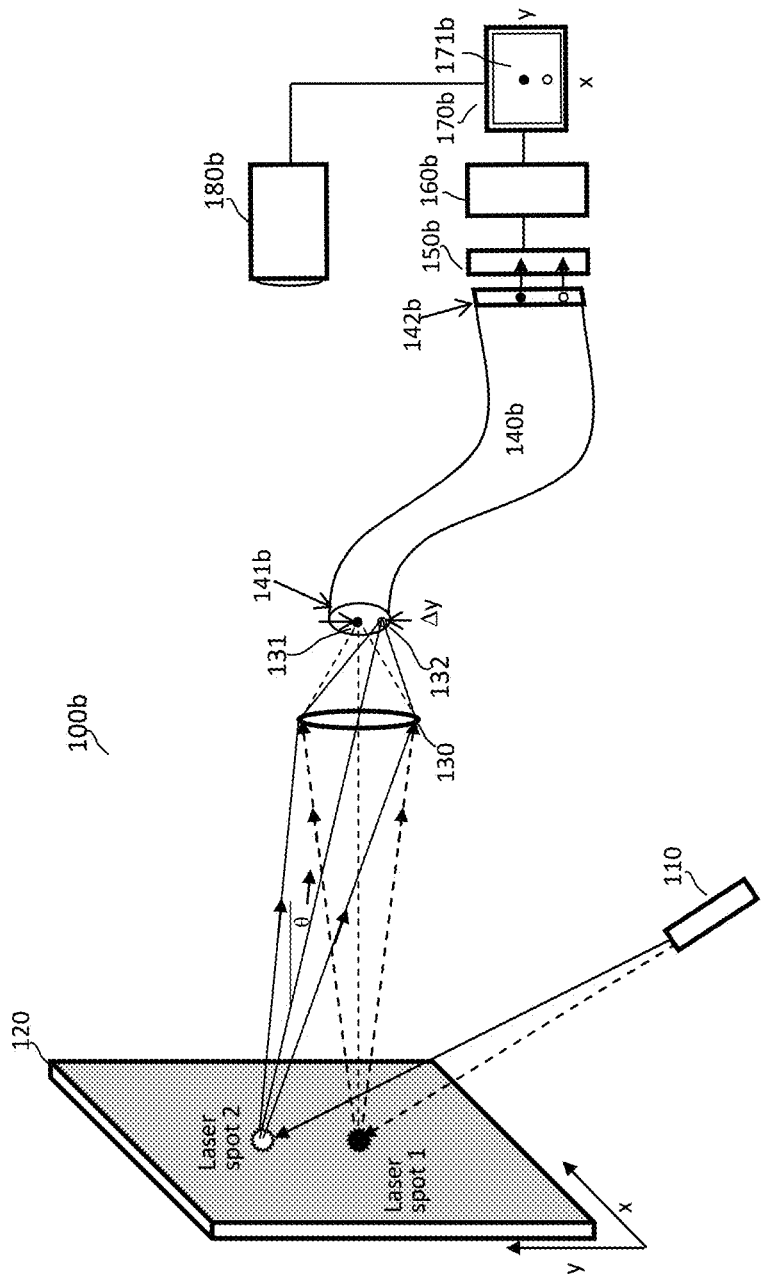
FIG. 1b shows a block diagram of an alternate system for determining location of a light spot on a surface using a linear detector array.

FIGS. 1a and 1b show a block diagram of a respective exemplary system (100a or 100b) for determining location of a light spot on a surface. Specifically, as commonly shown in FIGS. 1a and 1b, light emitted from a laser source 110 that is reflected and back-scattered from a surface 120 impinges on a lens 130 and is focused to a spot in the focal plane of the lens. A basic property of such a lens 130 is that the x and y positions of the focused spot, measured from the center of the lens (e.g., 130), are proportional to the $\theta_x$ and $\theta_y$ angles of the incident light relative to the optical axis of the lens:

$$x = f\theta_x \text{ and } y = f\theta_y,$$

where f is the lens focal length.

$\theta_x$ and $\theta_y$ angles of rays incident on the lens are proportional to the x and y position of the light spot on the target surface, as measured from the center axis through the lens. Therefore, the x-y position of the focused spot in the lens focal plane directly represents the x-y position of the laser spot in the target surface (e.g., 120). As an example, light spot 1 in FIGS. 1a and 1b is located on the center axis of the lens 130; light scattered from this location is collected by the lens 130 and focused into a spot 131 at the center of the focal plane of the lens 130. Light scattered from spot 2 is displaced vertically from the optical axis of the lens 130, and is focused by the lens 130 into a spot 132 that is vertically displaced by a distance of $y=f\theta_y$ in the focal plane of the lens.

In the general example 100a of FIG. 1a, the simplest method to determine the location of the laser spot in the target space surface 120 is to place a 2-dimensional detector array 150a against an output end 142a of the fiber bundle 140a outputting a 2D intensity distribution in the focal plane of the lens in FIG. 1a. The position of the spot formed by the lens 130 is then found by locating the centroid of a set of brightest illuminated pixels of the FPA of the detector 150a based on electronic signal processing (e.g., 160a) of the 2D intensity distribution output. The number of illuminated pixels depends on the FPA pixel size and the size of the focused spot, which in turn is determined by the focal length, diameter, optical quality of the lens 130, and the distance of the input end 141a of the fiber bundle from the focal plane of the lens. For short-wave infrared (SWIR) wavelengths near 1550 nm, the conventional Indium Gallium Arsenide (InGaAs) cameras with two dimensional detector arrays 150a are much more expensive than Silicon-based counterparts used for shorter wavelengths, have slow read-out rates, typically below 100 Hz, and have lower resolution, which provides a need for a lower cost and faster response spot tracking solution for the SWIR spectral band. Finally, in order to display the position of the light spot on the target surface 120, the output of the processor 160a provides an input to a 2-D image display 170a; the spot position is indicated on the display 170a by a small marker icon. The icon is superimposed on a context image 171a of the target surface 120. This context image 171a is provided by a camera 180a that is bore-sighted with the spot position sensor.

Alternatively, in FIG. 1b, we describe herein an alternate method to use one-dimensional InGaAs detector arrays, which are less complex and costly than two dimensional arrays, and have a faster overall readout rate; a feature required for discriminating short laser pulses from image clutter caused by sunlight. An exemplary embodiment of such an array is InGaAs linear photodiode array. (See, e.g., linear 1024-element InGaAs detector array described by Sensors Unlimited, Inc. in web link http://www.sensorsinc.com/downloads/SU1024LE.pdf.) In order to maintain the higher resolution and field-of-view capability of a 2D camera for spot location, we also describe a method for processing the 1D linear array data to provide high-resolution spot location. This position processing is similar to the method described in U.S. Pat. No. 8,493,573 B2 issued to Chinn et al. on Jul. 23, 2013, but without the need to fabricate a specially configured sparse 2D detector array for placement near the lens focal plane.

FIG. 1b shows a block diagram of such an alternate system 100b for determining location of a light spot on a surface using a linear detector array 150b. Conversion from a 2D area near the focal plane of the input pupil lens 130 to a linear geometry at the InGaAs detector array 150b is accomplished by using an alternate fiber bundle 140b, shown in FIG. 1b. The input end 141b of the alternate fiber bundle 140b is placed near the back focal plane of a light collecting lens 130. The alternate fiber bundle 140b can be comprised of multiple individual fibers, or alternatively, multiple sub-bundles, each sub-bundle being based on multiple individual fibers. The bundle transforms a circular, hexagonal, or similar 2D area at its input end 141b into a long rectangular area at its output end 142b; light emerging from the output end 142b impinges onto a linear InGaAs detector array 150b as shown in FIG. 1b. The position of the light spot on the linear detector array 150b uniquely represents the position of a light spot incident on the 2D input end 141b of the alternate bundle 140b and therefore the x-y position of the light spot on the target surface 120; there is a one-to-one relationship between a specific x-y position of the light spot on the target 120 and location of illuminated detector pixels on the linear detector array 150b. Light power received by each pixel is represented in the electrical signal from the serial readout circuit of detector array 150b. The electrical signals from all pixels are fed into an electronic processor 160b in FIG. 1b, which maps the position of each illuminated linear array pixel into a 2D, x-y position of the corresponding fiber sub-bundle near the lens focal plane (e.g., 141b). Thereby, the processor finds the x-y position of the light spot on the 2D input end 141b of the alternate bundle 140b, and therefore the x-y position of the light spot on the target surface 120. In order to display the position of the light spot on the target surface 120, the output of the processor 160b provides an input to a 2-D image display 170b; the spot position is indicated on the display 170b by a small marker icon. The icon is superimposed on a context image 171b of the target surface 120. This context image 171b is provided by a camera 180b that is bore-sighted with the spot position sensor. Alternately, a see-through display can be used in conjunction with a direct-view optical sight that allows an observer to directly view the target surface.

Figure 2:
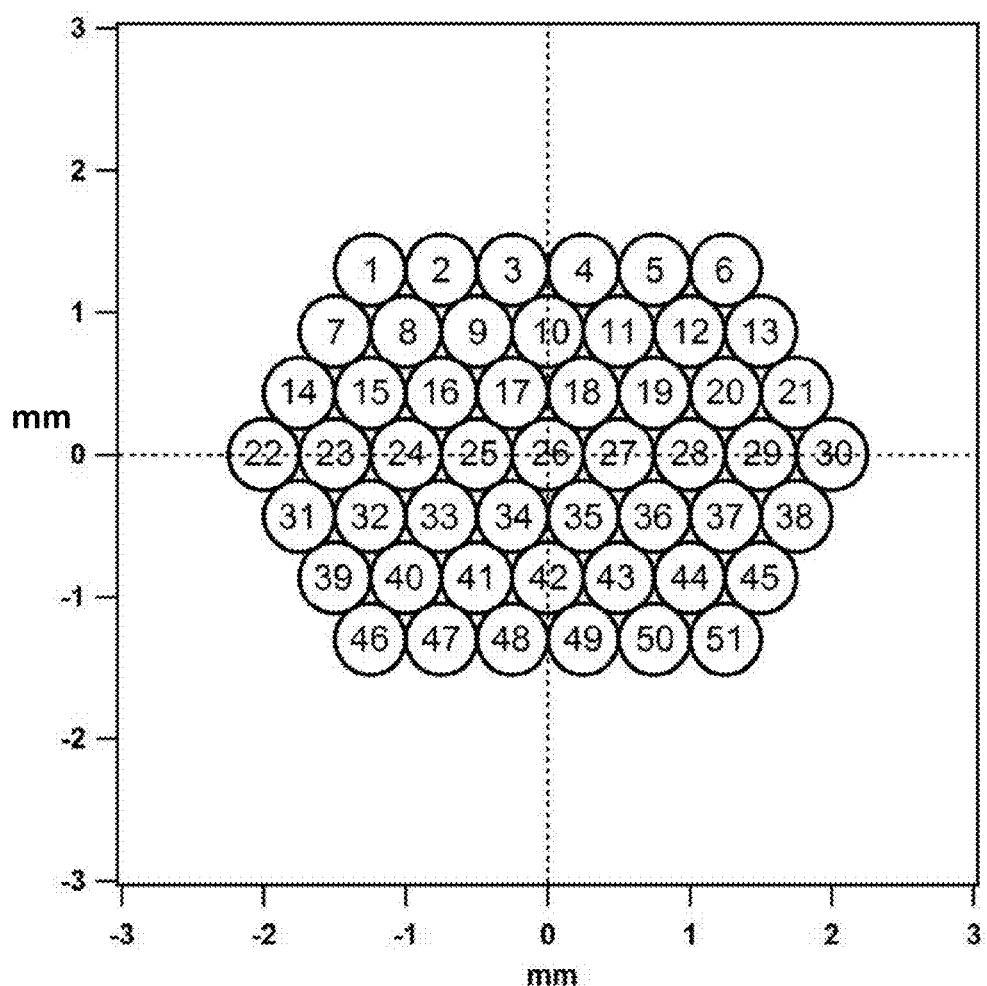
FIG. 2 shows an input end of an exemplary fiber bundle, comprising a 2D array of 51 sub-bundles, in the focal plane of lens.

As an example of such an alternate fiber bundle 140b, let each sub-bundle have a circular cross section with a diameter of 0.5 mm diameter, and be made up of 50 µm diameter fibers. For closely packed fibers, a 0.5 mm-diameter circle can hold ~85 fibers, which comprise a sub-bundle. (See, e.g., an exemplary sub-bundle 343 comprising about 85 fibers in FIG. 3.) An example of a 2D array comprising 51 of such fiber sub-bundles is shown in FIG. 2, where the total array width is 4.5 mm. Specifically, FIG. 2 shows an input end 141b of an exemplary fiber bundle (e.g., 140b), comprising a 2D array of 51 sub-bundles, near the focal plane of lens 130. In this instance no finer scale fiber arrangement within a mini-bundle is done, so the smallest effective detection element in the focal plane is the 0.5 mm-diameter circular sub-bundle (e.g., 1-51). This configuration combines the features of a limited number of fiber sub-bundles of large diameter (0.5 mm) with the mechanical flexibility of the small 50 µm diameter fibers. Larger diameter sub-bundles (e.g., 1-51) and larger 2D arrays of sub-bundles provide a larger field of view for the laser spot location.

Figure 3:
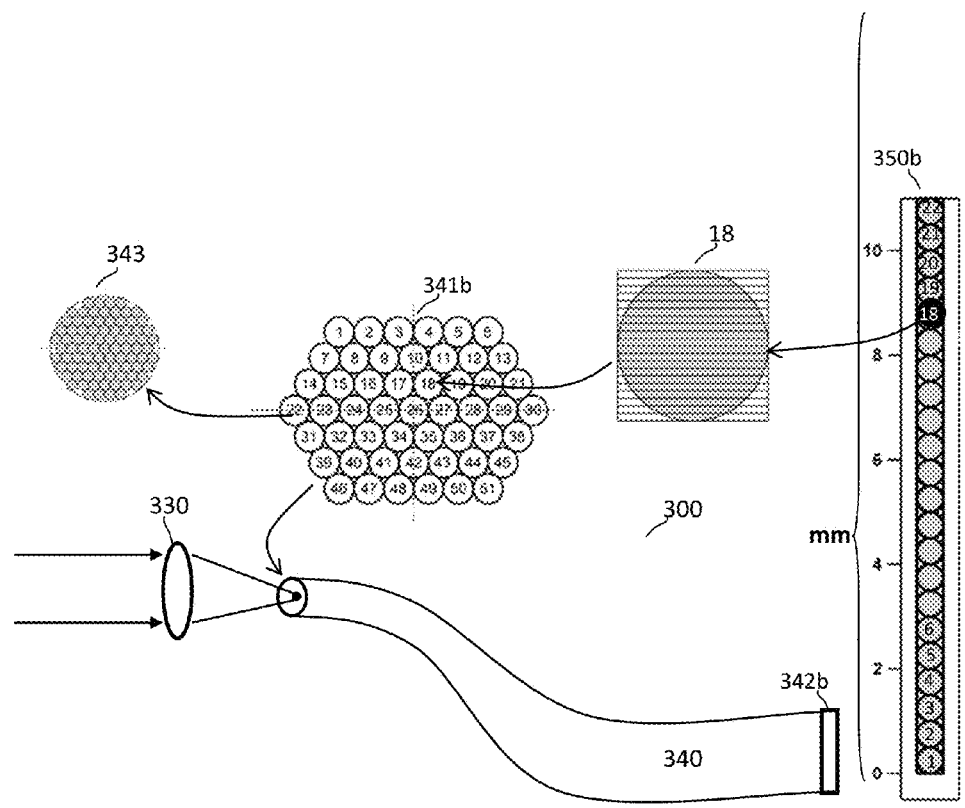
FIG. 3 shows a configuration of an exemplary optical system showing the focusing lens and the fiber bundle, comprising 51 sub-bundles, for converting the 2D light collection area into a linear area which matches the detector array.

FIG. 3 shows a configuration of an exemplary optical system 300 showing a focusing lens 330 and an exemplary fiber bundle 340, comprising 51 sub-bundles, for converting a 2D light collection area 341b into a linear area 342b which matches the detector array. FIG. 3 shows that the bundle arrangement changes to a linear array at its far end 342b facing the linear detector array 350b. As shown in FIG. 3, a 0.5 mm diameter sub-bundle 18 is depicted as enlarged to correspond to a sub-bundle 18 in a linear pattern overlay of the linear array 350b, wherein the numeric legend to the left depicts the scale in millimeters of a partial bottom portion of the 25.5 mm linear detector array 350b. A typical commercially available linear sensor array has 1024 detector elements (pixels) on 25 µm pitch with 0.5 mm width, and 25.6 mm total length. (See, e.g., linear 1024-element InGaAs detector array described by Sensors Unlimited, Inc. in web link http://www.sensorsinc.com/downloads/SU1024LE.pdf, incorporated herein by reference.) As depicted, a 0.5 mm diameter sub-bundle can illuminate 20 linear pixels of the linear detector array 350b. In order to achieve a higher fill factor for the set of pixels 18 in the linear array in FIG. 3, alternately the sub-bundle end facing the detector array can have a square cross section. When the 51 sub-bundles in FIG. 2 are arranged into a linear array (e.g., 342b of 340), its total length of 25.5 mm matches the length of the exemplary linear detector array 350b. FIG. 3 shows an exemplary case where the position of fiber sub-bundles in the linear array, 350b, follow the sequential numerical order of fiber sub-bundles in the 2-D end of the fiber array, 341b. It should be understood, however, that the fiber sub-bundles can be placed at random positions in the linear array, 350b. The only requirement is that it should be known which fiber sub-bundle at the linear array end 350b corresponds to which fiber sub-bundle at the 2D array end. A single 0.5 mm fiber sub-bundle matches the detector width and covers 20 of the 25 μm×500 μm detector elements, exemplified as sub-bundle 18 in FIG. 3. Light from each sub-bundle (e.g, 1-51) couples into contiguous group of 20 detector elements in the linear detector array 350b, and the electrical output of these 20 elements can be added electrically to produce a single electrical output that is proportional to the total optical power from the sub-bundle. As an example, light coupled into sub-bundle #18 in the 2D array of 51 sub-bundles (e.g., 341b) couples into a section of the linear array 350b positioned between 8 mm and 9 mm from one end of the detector array, as shown in FIG. 3. With this arrangement, the entire linear detector array 350b then maps into the 2D array of 51 circular sub-bundle areas 341b at the lens focal plane, making it possible to determine laser spot position within a 2D field of view of the lens 330 and 2D array 341b.

In a preferred embodiment, the spot incident on the 2D array 341b is larger than the size of a single sub-bundle. This allows light to couple into several neighboring sub-bundles (e.g., 1-51). By comparing the powers coupled into the multiple neighboring bundles, the center of the focused light spot can be determined with greater precision than if all of the light were coupled in a single bundle. The size of the focused spot is increased by moving the input end of the 2D bundle away from the focal plane of the lens, causing the spot to become de-focused.

Figure 4:
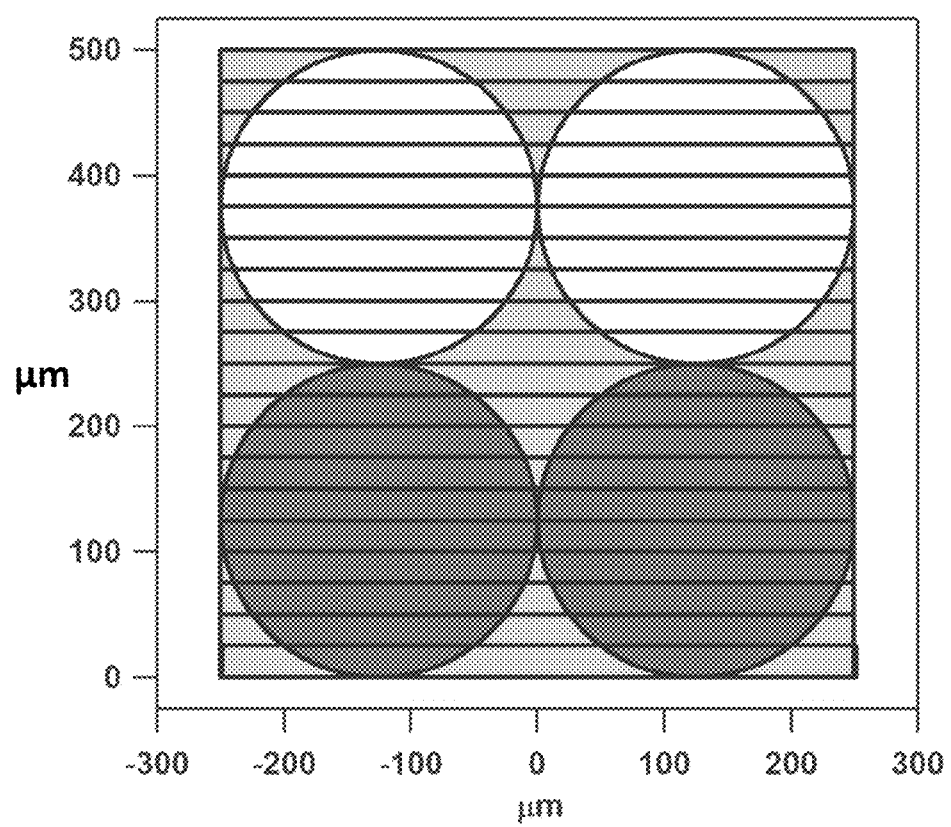
FIG. 4 shows an exemplary micro-bundle coupling of fibers to linear array.

An alternative to the use of sub-bundles exists; it is more difficult to fabricate, but can yield a larger number of smaller detection elements in the focal plane, and provide the possibility of higher resolution location of the spot. For convenience and ease of construction, special larger diameter individual fibers are used, with the diameter chosen to be small enough to retain fiber flexibility. To obtain higher spatial resolution, these large diameter fibers are arranged in a periodic 2D array near the lens focus and then separated to provide an ordered, narrow rectangular bundle that matches the narrow linear geometry of the linear detector array. There is a predetermined sequence of the narrow bundle portion such that each detector element of the linear array, which is illuminated by several fibers, can be associated with a single contiguous region of the 2D input bundle. For example, we choose a fiber diameter of 250 μm, and create high-resolution elements by choosing pairs of adjacent fibers. Each pair of fibers couples light to 10 sequential pixels of the same linear array example given above. This is illustrated in FIG. 4. Specifically, FIG. 4 shows exemplary micro-bundled pairs of fibers. The electrical signals from these 10 pixels are added together, providing one electrical signal from each ordered pair of fibers. In this figure, the depicted gray shades only signify that common-shaded pairs form a single micro-bundle whose position is known in the focal plane. In this arrangement approximately 100 detection elements are provided in the focal plane of the light collection lens, twice as many as with the 0.5 mm sub-bundles in FIG. 2.

For efficient light transmission, fiber used in this application should be multimode with relatively thin cladding and a high numerical aperture to assure light gathering from a large range of light incidence angles. The fibers should also have minimum transmission loss near 1.5 μm wavelength.

Figure 5:
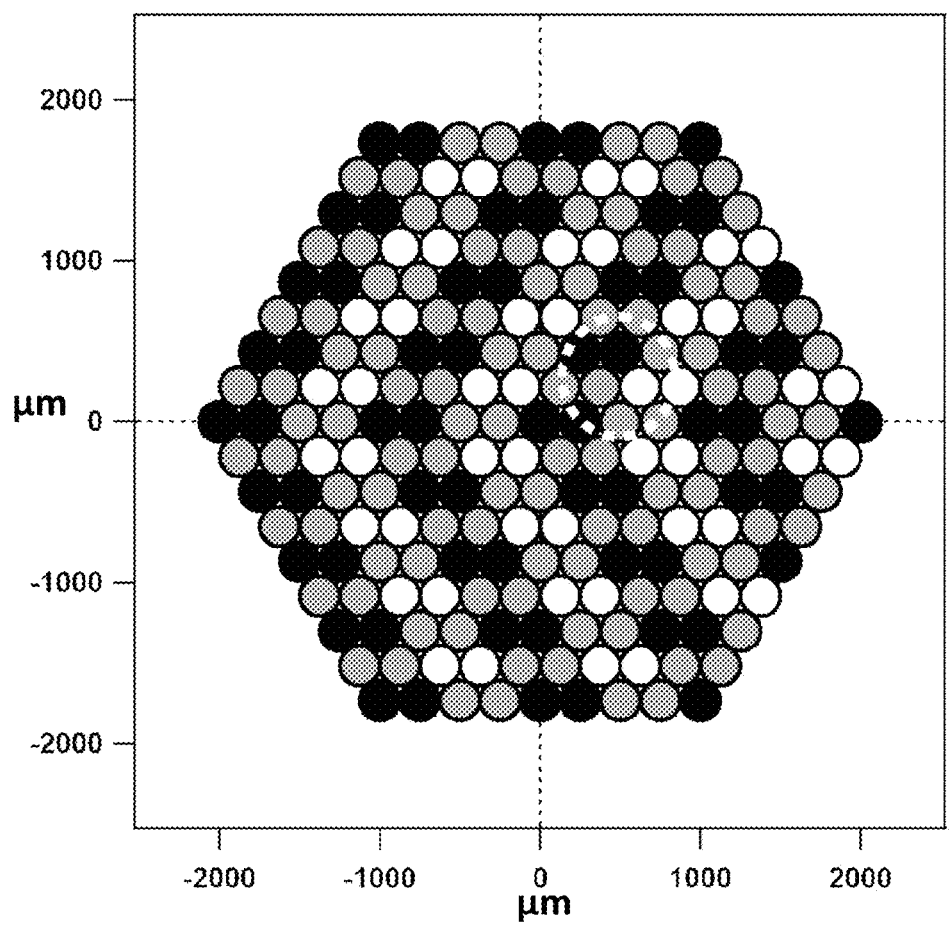
FIG. 5 shows an exemplary HCP fiber pair arrangement having an angular orientation, wherein a white dashed circle exemplifies the size of a defocused light spot.

An example of a hexagonal close-packed (HCP) fiber array in the lens focal plane is shown in FIG. 5. Specifically, FIG. 5 shows an exemplary HCP fiber pair arrangement, wherein commonly-shaded pairs have a common angular orientation. A white dashed circle exemplifies the size of an exemplary defocused light spot. The gray-shades are only an aid to visualizing which pairs of fibers are selected for the micro-bundles. In this instance, the pairs with common shadings are selected along adjacent rows, starting from the left; all pairs are oriented horizontally. This design also allows for configuration flexibility. For example, one can make the micro-bundles comprising adjacent 2-pair rhombohedra, thus forming a four-fiber micro-bundle.

The example in FIG. 5 shows 271 fibers, of which 204 (102 pairs) can be matched to the linear detector array. The light spot generated by the lens, and shown in FIG. 5 as dashed white line circle, is sufficiently large to illuminate several contiguous fibers.

With signal processing, this sensor system can determine the spot location (as a coordinate in the focal plane) with higher resolution than that of an individual mini- or micro-bundle. To achieve this, the optical spot must overlap several adjacent bundles, and provide different electrical signals from the corresponding regions of the linear array detectors. By displacing the fiber bundle array sufficiently from the lens focal plane, the optical intensity of the defocused spot will approximate a circular top-hat distribution, being in the geometric cone of the focused light rays. Typically the spot diameter should be at least 1.5 times the largest sub-bundle dimension, as is illustrated by the white dashed line in FIG. 5.

To locate the spot, one robust approach is to perform an optimization on the detector output signals that minimizes the error between the set of signals and the values expected from the estimated spot location. This is essentially the same as performing a maximum a posteriori estimate, well known in signal processing. Further description of this technique for similar sparse array optical processing is given in U.S. Pat. No. 8,493,573 B2 issued to Chinn et al. (U.S. Pat. No. 8,493,573 B2, issued on Jul. 23, 2013, and entitled, "High-resolution optical position sensing with sparse, low-resolution detectors," is incorporated herein by reference.)

A further advantage of the linear detector array for this application is that it may operate much faster than a 2D camera because each detector can be connected to an individual preamplifier. Depending on the readout integrated circuit, up to $10^7$ pixels per second may be read out. This corresponds to 10 kHz (1D) frame rate, useful for dynamic synchronization with pulsed signals. The high frame rate is also useful for discriminating short light pulses, such as generated by a Q-switched laser (typically 10-30 ns long) from sunlit clutter in the field of view.

It is obvious that many modifications and variations of the present invention are possible in light of the above teachings. It is therefore to be understood that within the scope of the appended claims, the invention may be practiced otherwise than as described.

What is claimed is:

1. A method for determining the position of a light spot generated by an optical beam when it falls on a scattering surface using a detector array, comprising the steps of:
    emitting light from a laser source towards a surface to reflect and backscatter the emitted light incident on the surface;
    focusing said backscattered light incident on a lens to a spot in a focal plane of the lens;

disposing a fiber bundle with its input end near the focal plane of the lens;

placing a detector array against an output end of the fiber bundle outputting 2D intensity distribution in the focal plane to produce a corresponding set of electrical signals;

electronic signal processing the set of electrical signals to provide high-resolution spot location, wherein a position of the focused spot formed by the lens is determined based on finding a centroid of a set of the brightest illuminated pixels of the detector array;

a bore-sight aligned camera providing a context image; and displaying the location of the spot on a display of said context image based on said electronic signal processing of said set of electrical signals, wherein a coordinate position of the focused spot is proportional to $\theta_x$ and $\theta_y$ and e angles of the incident light relative to an optical axis of the lens, wherein the coordinate position is determined as $$x = f\theta_x \text{ and } y = f\theta_y,$$

where f is a focal length of the lens.

2. The method for determining the position of a light spot recited in claim 1, wherein short-wave infrared wavelengths near 1550 nm is used for the emitted light to illuminate a variable number of pixels.

3. The method for determining the position of a light spot recited in claim 1, wherein the detector array is a one-dimensional detector array to provide a one-dimensional linear array data for high-resolution spot location.

4. The method for determining the position of a light spot recited in claim 1, wherein a two-dimensional set of multiple individual fibers at the input end of the fiber bundle is rearranged at the output end to a linear geometry.

5. The method for determining the position of a light spot recited in claim 1, wherein said fiber bundle is comprised of multiple sub-bundles, each sub-bundle being based on multiple individual fibers.

6. A system for determining the position of a light spot generated by an optical beam when it falls on a scattering surface, comprising:

a laser source for emitting light towards a surface to reflect and backscatter the emitted light;

a lens disposed to focus said backscattered light to a spot in a focal plane of the lens;

a fiber bundle with its input end disposed near the focal plane of the lens, an output end of the fiber bundle being arranged to output a 2D intensity distribution in the focal plane mapped to a linear geometry at its output end, wherein said fiber bundle is comprised of 0.5 mm diameter sub-bundles, a sub-bundle being comprised of closely packed fibers of 50 µm diameter each;

a linear detector array disposed to mate with said output end of the fiber bundle and output one-dimensional linear array data as a set of signals that represent the intensity distribution in the focal plane of the lens;

an electronic signal processor to process the one-dimensional linear array data for high-resolution spot location; and a display for imaging said surface in an x-y position display field of view, wherein a position of the spot is indicated by a marker icon on the display based on the processed one-dimensional linear array data.

7. The system for determining the position of a light spot generated by an optical beam according to claim 6, wherein the linear detector array is an InGaAs linear photodiode array or an InGaAs detector array.

8. The system for determining the position of a light spot generated by an optical beam according to claim 6, wherein said fiber bundle has a 2-dimensional input end mapped to a linear fiber bundle arrangement at its output end, wherein the input end of the fiber bundle is placed near a back focal plane of said lens.

9. The system for determining the position of a light spot generated by an optical beam according to claim 6, wherein said fiber bundle is comprised of multiple individual fibers, or alternatively, multiple sub-bundles, each sub-bundle being based on multiple individual fibers.

10. The system for determining the position of a light spot generated by an optical beam according to claim 9, wherein the one-dimensional linear array data corresponding to signals from all pixels are processed by said electronic signal processor to map the position of each illuminated linear array pixel into a two-dimensional x-y position of the corresponding fiber or sub-bundle near the lens focal plane and determine an x-y position of the light spot.

11. The system for determining the position of a light spot generated by an optical beam according to claim 6, wherein said fiber bundle rearranges its fibers at its circular or hexagonal input end into fibers terminating as an elongated rectangular output end.

12. The system for determining the position of a light spot generated by an optical beam according to claim 6, wherein a light spot on the target illuminates corresponding detector pixels on the linear detector array.

13. The system for determining the position of a light spot generated by an optical beam according to claim 6, wherein the icon is superimposed on a context image of the target surface provided by a bore-sight aligned camera.

14. The system for determining the position of a light spot generated by an optical beam according to claim 6, wherein a see-through display is used in conjunction with a direct-view optical sight that allows an observer to directly view the target surface.

15. The system for determining the position of a light spot generated by an optical beam according to claim 6, wherein a fiber bundle has 51 sub-bundles of about 85 fibers each, an output end of each sub-bundle facing the linear detector array uniquely having a square shaped cross section.

16. A system for determining the position of a light spot based on a hexagonal close-packed fiber array, comprising:

a lens disposed to focus light to a focal plane of the lens;

a hexagonal close-packed fiber array with its input end disposed near the focal plane of the lens, wherein pairs of adjacent fibers at the input end form micro-bundles to output an image in the focal plane mapped to a linear geometry of sequenced micro-bundles at its output end; and a linear detector array disposed to mate with said linear geometry of sequenced micro-bundles, wherein a pair of fibers at the output end couples to a respective set of sequential pixels of said linear detector array to output one-dimensional linear array data in sets of sequential pixels as an image signal output for electronic signal processing to determine the position of the light spot, wherein each micro-bundle is comprised of a respectively adjacent 2-pair rhombohedra at the input end, thus forming a four-fiber micro-bundle at the output end.

17. The system for determining the position of a light spot based on a hexagonal close-packed fiber array according to claim 16, wherein a fiber is a multimode fiber of 250 µm fiber diameter with thin cladding, having a high numerical aperture and a minimum transmission loss near 1.5 μm wavelength.

\* \* \* \* \*